US008795205B2

(12) United States Patent
Maity et al.

(10) Patent No.: US 8,795,205 B2
(45) Date of Patent: Aug. 5, 2014

(54) OPTICAL DISPLACEMENT SENSOR AND APPARATUS FOR MEASURING DISPLACEMENT

(75) Inventors: Sandip Maity, Bangalore (IN); Kunal Ravindra Goray, Munich (DE); Nasir Ahmed Desai, Bangalore (IN); Kiran Kumar Bogineni, Bangalore (IN); Sampa Ghosh, Bangalore (IN); Rachit Sharma, Bangalore (IN)

(73) Assignee: General Electric Company, Niskayuna, NY (US)

( * ) Notice: Subject to any disclaimer, the term of this patent is extended or adjusted under 35 U.S.C. 154(b) by 525 days.

(21) Appl. No.: 13/097,908

(22) Filed: Apr. 29, 2011

(65) Prior Publication Data

US 2012/0277631 A1    Nov. 1, 2012

(51) Int. Cl.
*A61B 5/103* (2006.01)
*A61B 5/117* (2006.01)
*G01B 11/06* (2006.01)
*A61B 5/107* (2006.01)
*G01B 11/00* (2006.01)
*A61B 5/00* (2006.01)
*G01B 11/02* (2006.01)

(52) U.S. Cl.
CPC .......... *G01B 11/0608* (2013.01); *A61B 5/1076* (2013.01); *G01B 11/00* (2013.01); *A61B 5/103* (2013.01); *A61B 5/435* (2013.01); *G01B 11/026* (2013.01); *A61B 5/4356* (2013.01); *A61B 2562/0233* (2013.01)
USPC ........................... 600/591; 600/587; 600/588

(58) Field of Classification Search
CPC ...... A61B 5/103; A61B 5/1076; A61B 5/435; A61B 5/4356; G01B 11/00
USPC ............................ 600/587, 588, 591
See application file for complete search history.

(56) References Cited

U.S. PATENT DOCUMENTS

| 4,860,768 A | 8/1989 | Hon et al. |
| 5,195,536 A * | 3/1993 | Silva et al. ............... 600/595 |
| 5,673,708 A * | 10/1997 | Athanasiou et al. .......... 600/587 |
| 5,876,357 A * | 3/1999 | Tomer ........................ 600/591 |
| 6,169,913 B1 | 1/2001 | Hojaiban et al. |
| 2004/0125382 A1* | 7/2004 | Banks ........................ 356/614 |
| 2005/0049509 A1* | 3/2005 | Mansour et al. ............ 600/476 |
| 2010/0191125 A1* | 7/2010 | Foged et al. ................ 600/476 |

FOREIGN PATENT DOCUMENTS

| EP | 1452139 A1 | 9/2004 |
| EP | 1852058 A1 | 11/2007 |
| WO | 9926537 A1 | 6/1999 |

OTHER PUBLICATIONS

K. F. Tham, S. Arulkumaran, S. Chua, C. Anandakumar, P. Singh, S. S. Ratnam; Abstract : A Comparison between Fibreoptic and Catheter-Tip Bridge Strain Gauge Transducers for Measurement of Intrauterine Pressure in Labour; URL : http://onlinelibrary.wiley.com/doi/10.1111/j.1447-0756.1991.tb00255.x/abstract; Asia-Oceania Journal of Obstetrics and Gynaecology vol. 17, Issue 1, pp. 83-87, Mar. 1991; 3 Pages.
* cited by examiner

*Primary Examiner* — Devin Henson
(74) *Attorney, Agent, or Firm* — Robert M. McCarthy

(57) ABSTRACT

An optical displacement sensor is provided according to one embodiment. The optical displacement sensor comprises a housing; a displacement member coupled to the housing, configured to contact an object under test and move based on displacement of the object under test; a light emitter coupled to the housing; an optical transducer coupled to the housing; and a reflecting surface coupled to the displacement member to reflect at least a part of the light emitted from the light emitter to the optical transducer, such that movement of the displacement member modifies intensity distribution of the light reflected to the optical transducer.

21 Claims, 4 Drawing Sheets

OPTICAL DISPLACEMENT SENSOR AND APPARATUS FOR MEASURING DISPLACEMENT

BACKGROUND

Embodiments presented herein relate generally to displacement sensors, and more specifically to optical displacement sensors.

Displacement sensors are used to sense and measure displacement of an object relative to another object, or the mean position of the object. Displacement sensors may be used to measure vibration intensity and frequency of the object being monitored. One known type of displacement sensor is the linear variable differential transformer (LVDT) based displacement sensor. An LVDT typically has three solenoid coils disposed end-to-end around a shaft—a primary coil at the middle, and two secondary coils on both sides of the primary coil. Displacement is measured as a differential signal generated due to changes in mutual inductance linked with the secondary coils. A cylindrical ferromagnetic core attached to a shaft moves between the solenoid coils based on displacement of the shaft. The shaft is held in its mean position by a spring mechanism. Sensitivity and calibration of LVDT type displacement sensors depend primarily on the spring mechanism. Therefore, the sensor performance depends primarily on the manufacturing tolerance the spring mechanism, and coupling of the shaft to the spring mechanism.

In the medical community, displacement sensors may be used, for example, to monitor frequency and strength of uterine contractions of pregnant women, during delivery. Such a device is known as a tocodynamometer. In tocodynamometers, a membrane is coupled to the LVDT shaft, for accepting displacement inputs from, for example, the abdominal wall of the patient. With time, the membrane, and the spring mechanism experience permanent deformation, thus adversely affecting the sensitivity and calibration of the tocodynamometer.

While displacement sensors are known in the art, what is needed is a displacement sensor that overcomes these and other shortcomings associated with known displacement sensors.

SUMMARY

An optical displacement sensor is provided according to one embodiment. The optical displacement sensor comprises a housing; a displacement member coupled to the housing, configured to contact an object under test and move based on displacement of the object under test; a light emitter coupled to the housing; an optical transducer coupled to the housing; and a reflecting surface coupled to the displacement member to reflect at least a part of the light emitted from the light emitter to the optical transducer, such that movement of the displacement member modifies intensity distribution of the light reflected to the optical transducer.

An intrauterine displacement sensor is provided, according to one embodiment. The intrauterine displacement sensor includes a housing; a displacement member coupled to the housing, configured to contact an abdominal wall of a patient and move responsive to uterine contractions of the patient; a light emitter coupled to the housing; an optical transducer coupled to the housing; and a reflecting surface coupled to the displacement member to reflect at least a part of the light emitted from the light emitter to the optical transducer, such that movement of the displacement member modifies intensity distribution of the light reflected to the optical transducer.

An apparatus for measuring displacement is provided, according to one embodiment. The apparatus includes an optical displacement sensor as described above. The apparatus further includes a processor electronically coupled to the optical transducer for monitoring intensity distribution of light incident on the optical transducer and converting the monitored intensity distribution into a displacement quantity; and an output device electronically coupled to the processor to output the displacement quantity.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Various embodiments of an optical displacement sensor are described herein. The optical displacement sensor employs a light emitter to project light onto a reflecting/scattering surface of a displacement member. The reflecting/scattering surface reflects/scatters at least part of the light onto an optical transducer. The displacement member is configured to contact an object under test, and move with the displacement of the object under test. The movement of the displacement member causes the reflecting surface to modify intensity distribution of the light reflected to the optical transducer. An apparatus for measuring displacement using the optical displacement sensor is also described. The apparatus includes a processor to monitor the intensity distribution of light incident on the optical transducer. The processor then converts the monitored intensity distribution into a displacement quantity. As used herein, intensity distribution is the distribution of luminous intensity. Modifying intensity distribution of the light reflected to the optical transducer includes shifting the location of incidence of light on the optical transducer, changing the area of incidence of light on the optical transducer, changing the distribution of luminous intensity, or a combination thereof.

Figure 1:
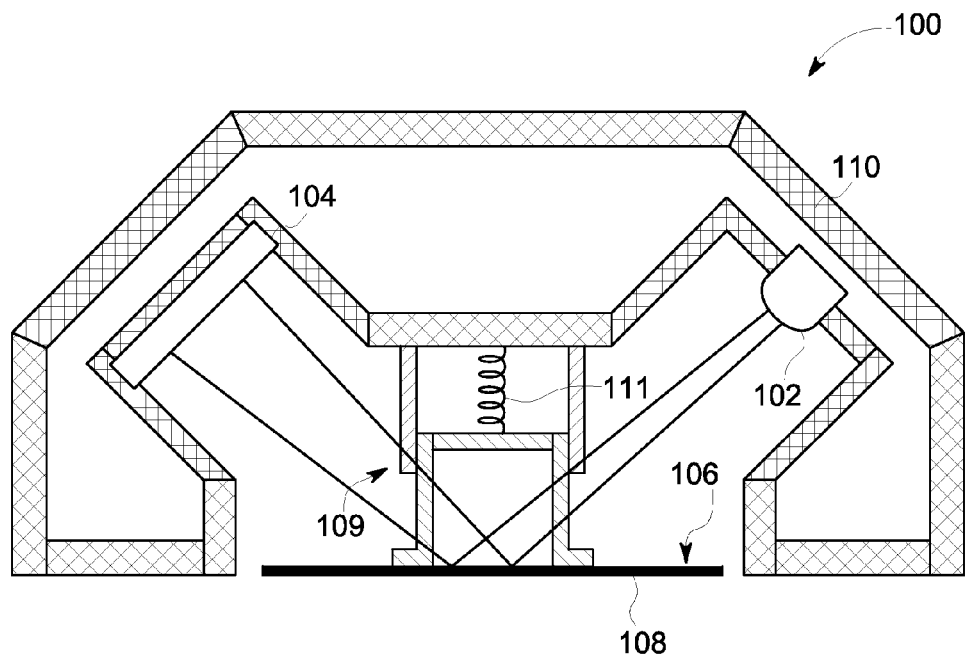
FIG. 1 illustrates an example optical displacement sensor, according to one embodiment.

FIG. 1 illustrates an example optical displacement sensor 100, according to one embodiment. The optical displacement sensor 100 includes a light emitter 102, an optical transducer 104, a reflecting surface 106, a displacement member 108, and a housing 110.

The light emitter 102 may include, without limitation, a light emitting diode (LED), an infrared emitter such as an IR LED, a laser source such as a laser diode, a broadband light source, a monochromatic light source, or an incandescent lamp. LEDs provide the advantage of low power consumption, light weight, and high luminous intensity. Laser sources such as laser diodes provide a highly directional light beam, and may improve the sensitivity of the sensor over other types of light emitters 102. The light emitter 102 projects light onto the reflecting surface 106. In some implementations, the light emitter 102 may project a beam of light onto the reflecting surface 106. In other implementations, the light emitter may project a pattern of light onto the reflecting surface 106. For example, a laser array type light emitter 102 may project a cross-hair or a grid pattern onto the reflecting surface 106.

The optical transducer 104 may include any transducer that converts incident light energy into a corresponding electrical signal. Example optical transducers 104 include, without limitation, image sensors such as charge coupled device (CCD) sensors, complementary metal oxide semiconductor (CMOS) sensors, photodiodes, scintillators, laser receivers, photoresistors, and phototransistors.

The light emitter 102 and the optical transducer 104 are chosen to complement one another. For example, a laser diode light emitter 102 may be used in combination with a laser receiver optical transducer 104. In various implementations, the optical transducer 104 may be an array type transducer. The optical transducer 104 may be in the form of a linear array, planar photodiode, position sensitive photodiode or a planar array. An array type optical transducer allows detection of shift in intensity distribution caused due to movement of the displacement member 108, and also provides data for measurement of the shift in intensity distribution of the incident light.

The reflecting/scattering surface 106 is designed to reflect at least a part of the light emitted from the light emitter 102 to the optical transducer 104. In some implementations, the reflecting surface 106 may be a substantially reflecting/scattering surface, such that the reflecting/scattering surface 106 causes very little reflection/scattering of incident light. In other words, the reflecting/scattering surface 106 may cause substantially specular reflection of the incident light. In such implementations, the reflecting surface 106 may be a highly polished, or a mirrored surface. Alternatively, the reflecting surface 106 may be a partially reflecting surface, such that the reflecting surface 106 reflects part of the incident light, and causes a high degree of scattering of the incident light. Simply stated, the reflecting surface 106 may cause diffuse reflection of the incident light. In such an implementation, the reflecting surface 106 may be a roughened surface, for example.

The reflecting surface 106 in one embodiment is coupled to the displacement member 108. The reflecting surface 106 may be a flat membrane made of a suitable reflective material, such as aluminum or acrylic film. The reflecting surface 106 may be bonded to the displacement member 108 using, for example, an adhesive. Alternatively, the reflecting surface 106 may be the inner surface of the displacement member 108. The inner surface of the displacement member 108 may be polished or mirrored to achieve the required reflecting and scattering properties. While described as fixedly coupled or otherwise attached in one embodiment, the reflecting surface 106 can be coupled to the displacement member 108 without being fixedly attached.

In one embodiment, the displacement member 108 may be a substantially rigid flat disc, or the like. The displacement member 108 may be constructed to resist bending or deformation under normal operating conditions. The displacement member 108 in another embodiment is flexibly coupled to the housing 110 using, for example, a flexible membrane, or a spring mechanism such as, but not limited to, a leaf spring or a coil spring. Specifically, the displacement member 108, for example, a flat disc is coupled to the housing 110 via a cylindrical shaft 109 and a spring 111. The spring 111 is disposed between the housing 110 and the cylindrical shaft 109. Alternatively, the displacement member 108 may be a flexible membrane itself. Such a displacement member 108 may be made of a suitable elastic material such that the displacement member 108 may deform during normal operating conditions, but return to its original shape while not in use.

The optical displacement sensor 100 senses displacement of the displacement member 108 through a shift in the intensity distribution of light reflected by the reflecting surface 106.

Figure 2:
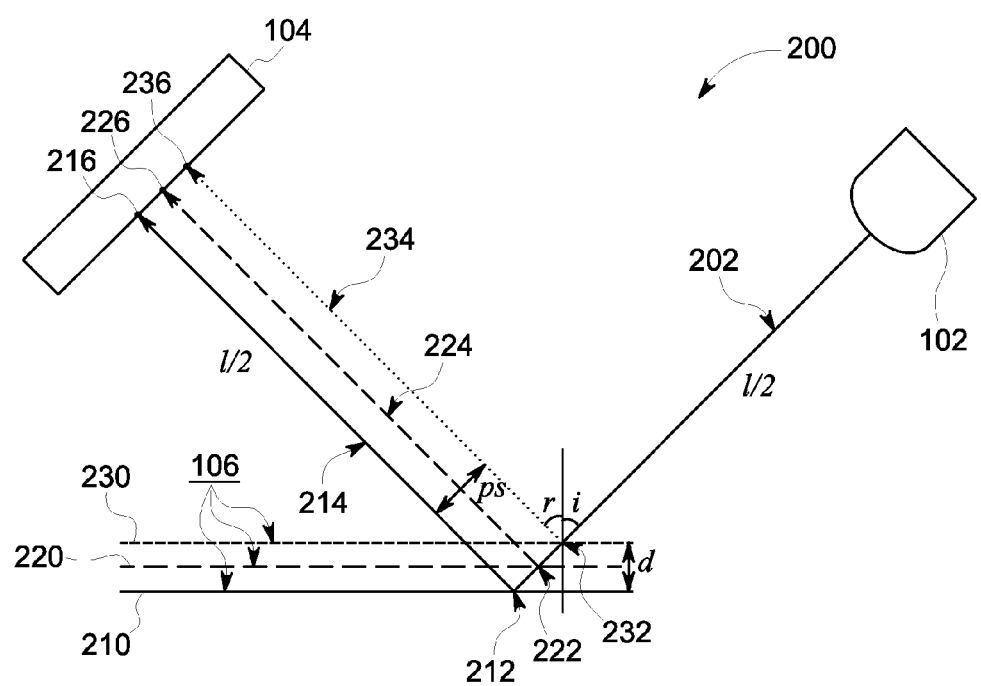
FIG. 2 illustrates a simplified ray diagram of the optics of an example optical displacement sensor, according to another embodiment.

FIG. 2 illustrates a simplified ray diagram 200 of the optical displacement sensor 100. The ray diagram 200 illustrates a single emitted ray 202 emitted from the light emitter 102, and incident on the reflecting surface 106. The reflecting surface 106 moves with the displacement member 108. Specifically, the cylindrical shaft 109 and the spring 111 (shown in FIG. 1) enable axial movement of the displacement member 108 when the displacement member 108 contacts an object under test. Ray diagram 200 illustrates the displacement member 108 in three positions, a mean position 210, a partially displaced position 220, and a fully displaced position 230. The light emitter 102 is coupled to the housing 110 such as attached or fixedly coupled. Therefore, the angle of incidence of emitted ray 202 on the reflecting surface 106 remains constant. However, the point of incidence of the emitted ray 202 on the reflecting surface 106 shifts with the displacement of the displacement member 108. The points 212, 222, and 232 illustrates the points of incidence on the reflecting surface 106 corresponding to positions 210, 220, and 230 respectively, of the displacement member 106. Following the law of reflection, the reflected rays 214, 224, and 234 are thus incident on the optical transducer 104 at points 216, 226, and 236 respectively. This shift in the point of incidence on the optical transducer 104 is proportional to the displacement of the displacement member 108. For instance, in ray diagram 200, the shift "ps" of the point of incidence on the optical transducer 104, is proportional to the displacement "d" of the displacement member 108.

Figure 3:
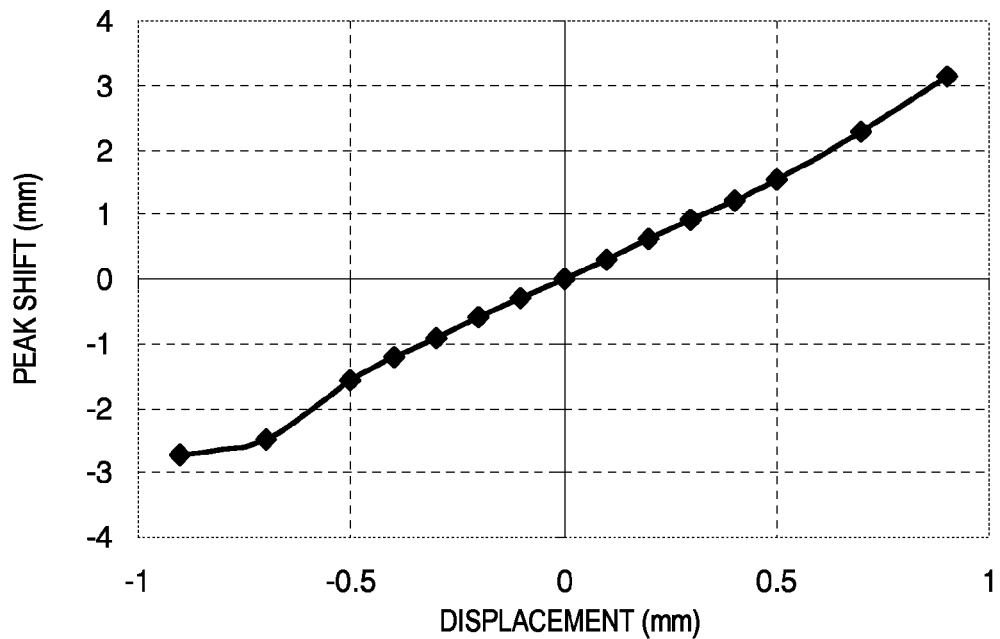
FIG. 3 is a graph of membrane displacement against the peak shift of intensity distribution of light incident on an optical transducer, according to one embodiment.

FIG. 3 illustrates an example graph of the relationship between displacement "d" of the displacement member 108 and the shift "ps" in the point of incidence on the optical transducer 104. Although FIG. 2 illustrates a single ray originating from the light emitter 102, it should be appreciated that in a real world implementation, the light emitter 102 emits a beam of light having a finite beam divergence. Simply stated, the light emitted is in the form of a cone of light, and has a finite area of incidence on the reflecting surface 106, and a finite area of incidence on the optical transducer 104. In such a scenario, the area of incidence on the optical transducer 104 shifts similar to the shift illustrated in the ray diagram 200. Further, the beam of light has peak intensity at the axis of the beam. Therefore, the displacement of the displacement member 108 may be computed by first detecting the intensity peak of the beam incident on the optical transducer 104, and then measuring the shift in the intensity peak.

Alternatively, the change in area of incidence may be used to measure the displacement of the displacement member 108. The area of incidence of the beam of light on the reflecting surface 106 and the optical transducer 104 depends on the geometric length of the path traversed by the beam. As seen in the ray diagram 200, displacement "d" of the displacement member 108 causes the geometric length "l" of the path traversed by the beam to change by 2 ps. Since the light emitter 102 remains the same, the beam divergence remains constant.

Figure 4:
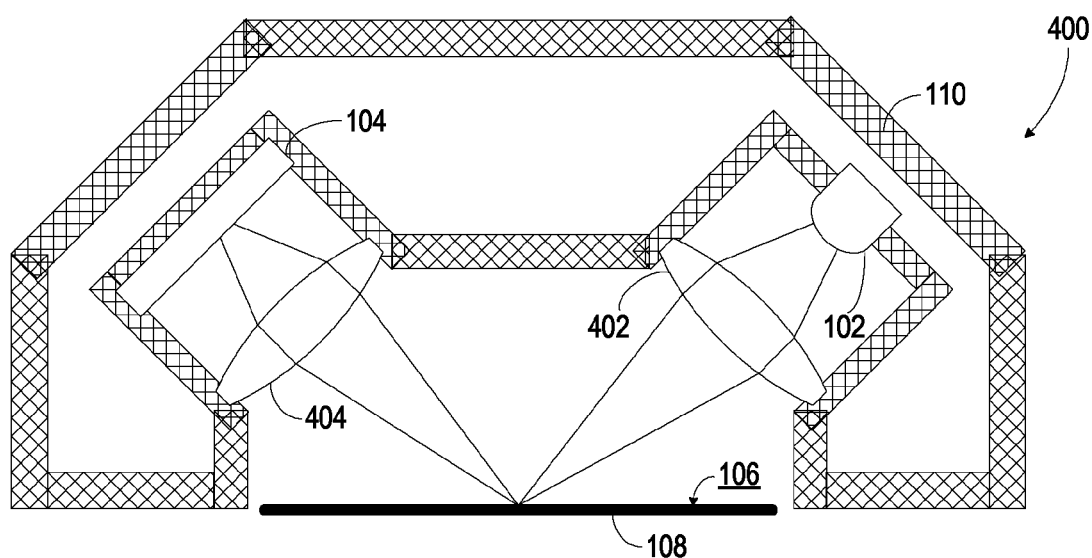
FIG. 4 illustrates an example optical displacement sensor, according to another embodiment.

In some embodiments, one or more lenses may be used to focus the beam of emitted light and the beam of reflected light. FIG. 4 illustrates an example optical displacement sensor 400 according to one such embodiment. The optical displacement sensor 400 includes a first lens 402, and a second lens 404, in addition to the light emitter 102, the optical transducer 104, the reflecting surface 106, the displacement member 108, and the housing 110. The first lens 402, and the second lens 404 may be aspheric lenses, to achieve a more accurate focusing. Alternatively, the first lens 402, and the second lens 404 may be spherical lenses. In some implementations, the first lens 402, and the second lens 404 may be Fresnel lenses.

The first lens 402 is arranged to focus the beam of light emitted by the light emitter 102 onto the reflecting/scattering surface 106. The second lens 404 is arranged to focus the beam of light reflected from the reflecting surface 106 onto the optical transducer 104. The first lens 402 may be arranged to focus the emitted beam of light substantially to a point on the reflecting surface 106, at the mean position 210 of the displacement member 108. The second lens 404 may be arranged to focus the beam of light reflected from the reflecting surface 106 substantially to a point on the optical transducer 104, at the mean position 210 of the displacement member 108.

Although FIG. 4 illustrates two lenses, in other embodiments, either of the two lenses may be used. Further, lens groups including multiple lenses may be used in place of either the first lens 402, the second lens 404, or both.

As the displacement member 108 displaces from the mean position, the emitted beam of light no longer converges to a point on the reflecting surface 106. Consequently, the reflected beam of light no longer converges to a point on the optical transducer 104, but to a small area of incidence. Similar to the embodiment described above in conjunction with FIG. 2, the change in area of incidence, and the shift in the area of incidence is proportional to the displacement "d" of the displacement member 108.

Thus, the change in intensity distribution of the light incident on the optical transducer 104 is used to detect displacement of the displacement member 108. As described above, the change in intensity distribution may be a shift in the peak of intensity distribution, a change in the area of incidence, a shift in the area of incidence, or a combination thereof.

Figure 5:
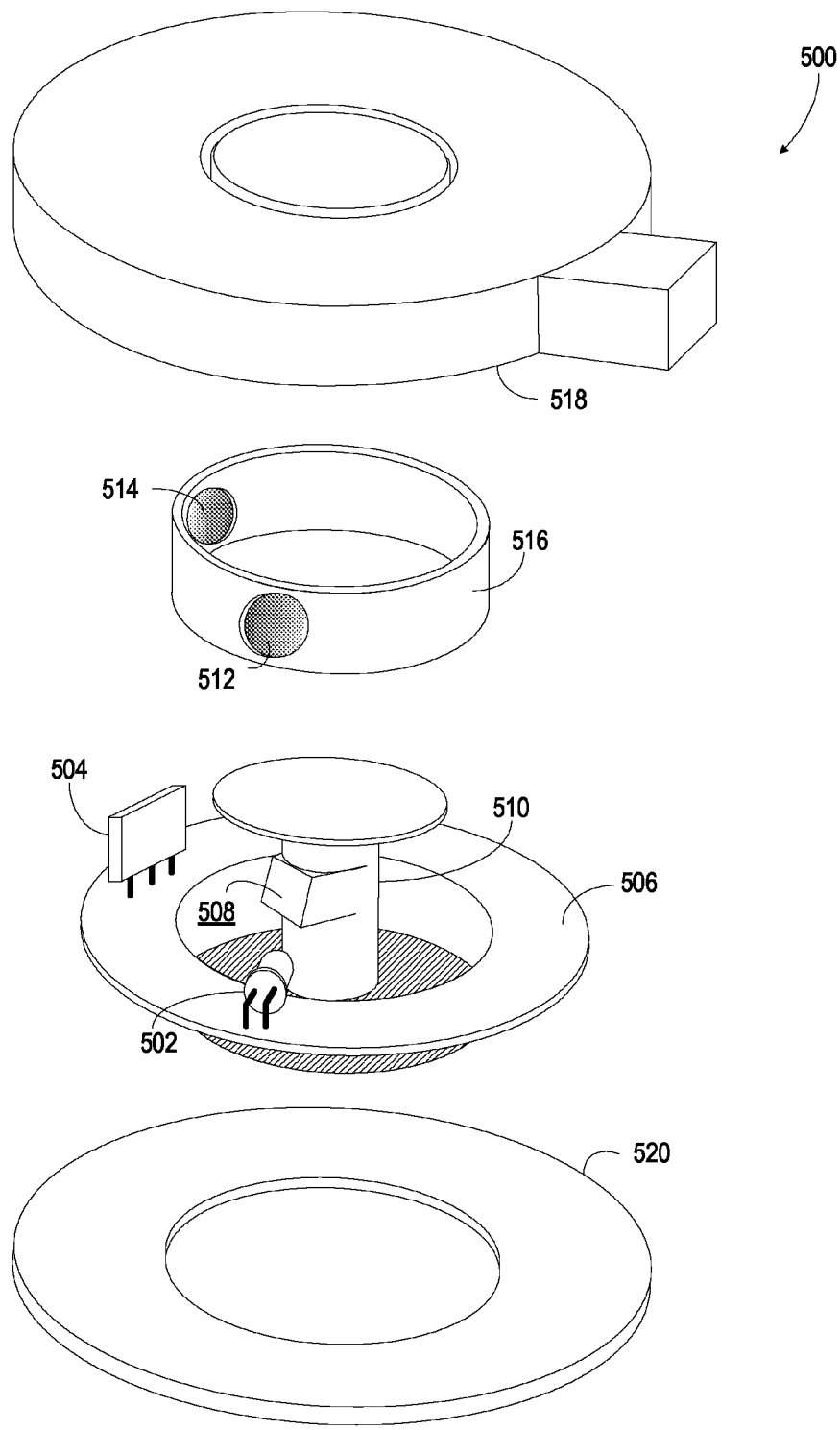
FIG. 5 illustrates an exploded view of an example optical displacement sensor, according to yet another embodiment.

FIG. 5 is an exploded view of an example optical displacement sensor 500, according to another embodiment. The optical displacement sensor 500 includes, a light emitter 502, an optical transducer 504, a printed circuit board (PCB) 506, a reflecting surface 508, a displacement member 510, a first lens 512, a second lens 514, a lens carrier 516, an upper housing component 518, and a lower housing component 520. The light emitter 502 and the optical transducer 504 are mounted on the PCB 506. The PCB 506 may be a through-hole type PCB, or a surface mount type PCB, depending on the packaging of the light emitter 502 and the optical transducer 504. The reflecting surface 508 is a wedge shaped implement disposed on the displacement member 510. The displacement member 510 is composed of a cylindrical shaft, for example, a flat disc disposed on one axial end of the cylindrical shaft, and a spring element on the other axial of the cylindrical shaft. The reflecting surface 508 and the displacement member 510 may be constructed as a single piece element. Alternatively, the reflecting surface 508 may be attached to the displacement member 510 using, for example, an adhesive, or a mechanical notch coupling. The first lens 512 is arranged to focus the beam of light emitted from the light emitter 502 onto the reflecting surface 508. The second lens 514 is arranged to focus the beam of light reflected from the reflecting surface 508 onto the optical transducer 504. The first lens 512 and the second lens 514 are coupled to the lens carrier 516.

The individual elements of the optical displacement sensor 500 function similar to the principle described in conjunction with FIGS. 1-4. Although FIG. 5 illustrates two lenses, in other embodiments, either of the two lenses may be used. Further, lens groups including multiple lenses may be used in place of either the first lens 512, the second lens 514, or both.

Figure 6:
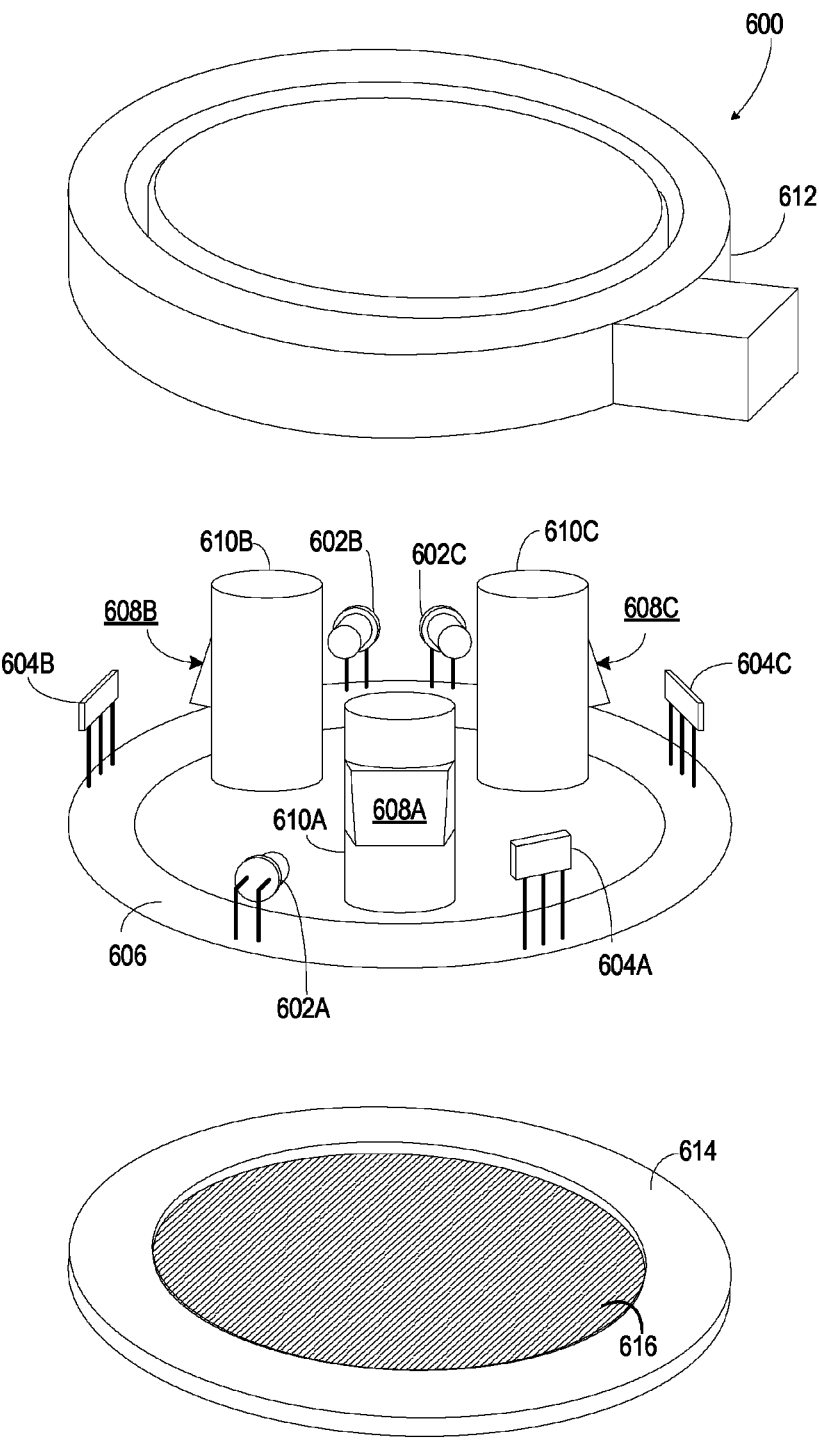
FIG. 6 illustrates an exploded view of an example optical displacement sensor, according to still another embodiment.

FIG. 6 illustrates yet another embodiment of an optical displacement sensor 600. The optical displacement sensor 600 includes, light emitters 602A, 602B, and 602C, optical transducers 604A, 604B, and 604C, a printed circuit board (PCB) 606, a reflecting surface 608A, 608B, and 608C, displacement members 610A, 610B, and 610C, an upper housing component 612, and a lower housing component 614. The light emitters 602 and the optical transducers 604 are mounted on the PCB 606. The displacement members 610A, 610B, and 610C are coupled to a contact plate 616. Such an optical displacement sensor 600 may be configured to also detect wobble movement of the contact plate 616, in addition to displacement of the contact plate 616. The sensed data from each of the optical transducers 604A, 604B, and 604C may be processed by a processor to compute a wobble movement of a contact plate 616. In some implementations, the optical displacement sensor 600 may include a lens assembly similar to that described in conjunction with FIG. 5 above. The lens assembly has not been show in FIG. 6 for reasons of clarity.

Other arrangements of the individual elements may also be possible without deviating from the scope of the invention.

In various embodiments, the optical displacement sensors 100, 400, 500, and 600 may be coupled to a processing module to monitor the intensity distribution of the light incident on the optical transducer. The optical transducer 104, 504, or 604 may be electronically coupled to a processor. The processor may be a mixed signal processor with a built-in analog to digital converter (ADC). In such an implementation, the output of the optical transducer 104, 504, or 604 may be coupled to the analog ports of the mixed signal processor. Alternatively, the processor may be a digital processor. The output of the optical transducer 104, 504, or 604 may be provided to an ADC. The digital output of the ADC may then be provided to the digital processor for monitoring the intensity distribution.

In one embodiment, the processor may monitor the shift in the peak of the light beam incident on the optical transducer 104, 504, or 604. The processor monitors the shift of the peak using periodic sampling, as a number of pixels of shift. The processor may then convert the monitored shift of the peak into a force measurement. Alternatively, the processor may convert the monitored shift of the peak into a displacement measurement, using the number of pixels of shift, and multiplying the number by a known pixel dimension of the pixels of the optical transducer 104, 504, or 604

In one implementation, the processor may periodically sample the intensity of light incident on each sensor site or pixel of the array type optical transducer 104, 504, or 604. The processor may then identify the sensor sites or pixels receiving a light intensity exceeding a predefined threshold—thus locating the peak of incident light. In another implementation, the processor may use peak finding algorithms to locate the peak of incident light. For example, the processor may compute a second derivative of the optical transducer data received from the optical transducer 104, 504, or 604. The processor may then apply smoothing to the second derivative to eliminate noise. The processor may then identify the peak as a maxima of the smoothed second derivative. In yet another implementation, the processor may use peak fitting algorithms to fit an expected intensity distribution profile, such as a Gaussian profile, to the optical transducer data, for locating the peak of incident light. The expected intensity distribution profile may be designed based on the light emitter 102, 502 or 602, and the reflecting surface 106, 508, or 608 used in the optical displacement sensor 100, 400, 500, or 600. The expected intensity distribution profile may be stored in the program code of the processor. Alternatively, the processor may have a calibration code programmed therein to detect the intensity distribution profile in a calibration mode. The intensity distribution profile thus detected may then be stored in the processor for use during normal operation. In still another implementation, the processor may compute a center of mass of the optical transducer data, thus locating the peak of incident light.

The processor may then convert the monitored shift of the peak into a force measurement. In one implementation, the processor has stored therein a look up table for converting the displacement measurements to force measurements. The look up table may be constructed based on known loads or forces applied to the displacement member 108, 510, or 610, during a calibration process. The look up table may include optical transducer voltage data mapped against the monitored shift of peak.

Further, the processor may also be configured to detect and measure the wobble movement for optical displacement sensor 600. The processor may compute the displacement of each displacement member 610A, 610B, and 610C individually, and then compute the wobble movement of the contact plate 616. The processor may use the known position of the displacement members 610A, 610B, and 610C on the contact plate 616, and the measured displacements to periodically compute an inclination of the contact plate 616. The processor may then use successively computed inclinations of the contact plate 616 to compute a wobble movement of the contact plate 616.

While the expected intensity distribution profile and the look up table have been described as stored on the processor, one skilled in the art will appreciate that either or both the expected intensity distribution profile and the look up table may be stored on a memory module external to the processor. The displacement measurements, the force measurements, or both may be presented through an output device. The output device may be an electronic display such as a liquid crystal display, or a cathode ray tube, or the like. Alternatively, the output device may be a printer to output the measurements onto a tangible medium such as paper. The output may be in the form of a graph plotted over a given time duration.

While the invention has been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

The invention claimed is:

1. An optical displacement sensor comprising:
   a housing;
   a rigid displacement member including a cylindrical shaft having a first end coupled to the housing via a spring and a second end having a flat disc, configured to contact an object under test and move based on displacement of the object under test;
   a light emitter coupled to the housing;
   an optical transducer coupled to the housing; and
   a reflecting surface coupled to the cylindrical shaft at a location between the first end and the second end to reflect at least a part of the light emitted from the light emitter to the optical transducer, such that movement of the flat disc modifies intensity distribution of the light reflected to the optical transducer.

2. The optical displacement sensor of claim 1 further comprising at least one of:
   a concentrating lens fixedly coupled to the housing, configured to focus light emitted from the light emitter onto the reflecting surface; and
   a collection lens fixedly coupled to the housing, configured to focus light reflected from the reflecting surface onto the optical transducer.

3. The optical displacement sensor of claim 1, wherein the light emitter is one of a light emitting diode (LED), an infrared emitter, a laser source, a broadband light source, a monochromatic light source, and a lamp.

4. The optical displacement sensor of claim 1, wherein the optical transducer is one of an image sensor, a charge coupled device, a CMOS sensor, a scintillator, a linear array photodiode, position sensitive photodiode and a planar array photodiode.

5. The optical displacement sensor of claim 1, wherein the reflecting surface comprises a reflective coating on one side of the flat disc.

6. The optical displacement sensor of claim 1, wherein the cylindrical shaft is a linearly displaceable shaft, and the reflecting surface comprises a wedge disposed on one longitudinal surface of the displaceable shaft.

7. The optical displacement sensor of claim 1, wherein the intensity distribution comprises at least one of a shift in a peak of the intensity distribution, a change in an area of incidence, and a shift in an area of incidence.

8. An intrauterine displacement sensor comprising:
   a housing;
   a rigid displacement member including a cylindrical shaft having a first end coupled to the housing via a spring and a second end having a flat disc configured to contact an abdominal wall of a patient and move responsive to uterine contractions of the patient;
   a light emitter coupled to the housing;
   an optical transducer coupled to the housing; and
   a reflecting surface coupled to the cylindrical shaft at a location between the first end and the second end to reflect at least a part of the light emitted from the light emitter to the optical transducer, such that movement of the flat disc modifies intensity distribution of the light reflected to the optical transducer.

9. The intrauterine displacement sensor of claim 8 further comprising at least one of:
   a concentrating lens fixedly coupled to the housing, configured to focus light emitted from the light emitter onto the reflecting surface; and
   a collection lens fixedly coupled to the housing, configured to focus light reflected from the reflecting surface onto the optical transducer.

10. The intrauterine displacement sensor of claim 8, wherein the light emitter is one of a light emitting diode (LED), an infrared emitter, a laser source, a broadband light source, a monochromatic light source, and a lamp.

11. The intrauterine displacement sensor of claim 8, wherein the optical transducer is one of an image sensor, a charge coupled device, a CMOS sensor, a scintillator, a linear array photodiode, a position sensitive photodiode and a planar array photodiode.

12. The intrauterine displacement sensor of claim 8, wherein the reflecting surface comprises a reflective coating on one side of the flat disc.

13. The intrauterine displacement sensor of claim 8, wherein the cylindrical shaft is a linearly displaceable shaft, and the reflecting surface comprises a wedge disposed on one longitudinal surface of the displaceable shaft.

14. An apparatus for measuring displacement comprising:
an optical displacement sensor comprising:
　a housing;
　a rigid displacement member including a cylindrical shaft having a first end coupled to the housing via a spring and a second end having a flat disc configured to contact an object under test and move responsive to displacement of the object under test;
　a light emitter coupled to the housing;
　an optical transducer coupled to the housing; and
　a reflecting surface coupled to the cylindrical shaft at a location between the first end and the second end to reflect at least a part of the light emitted from the light emitter to the optical transducer, such that movement of the flat disc modifies intensity distribution of the light reflected to the optical transducer;
a processor electronically coupled to the optical transducer for monitoring intensity distribution of light incident on the optical transducer and converting the monitored intensity distribution into a displacement quantity; and
an output device electronically coupled to the processor to output the displacement quantity.

15. The apparatus of claim 14, wherein the optical displacement sensor further comprises at least one of:
　a concentrating lens fixedly coupled to the housing, configured to focus light emitted from the light emitter onto the reflecting surface; and
　a collection lens fixedly coupled to the housing, configured to focus light reflected from the reflecting surface onto the optical transducer.

16. The apparatus of claim 14, wherein the light emitter is one of a light emitting diode (LED), an infrared emitter, a laser source, a broadband light source, a monochromatic light source, and a lamp.

17. The apparatus of claim 14, wherein the optical transducer is one of an image sensor, a charge coupled device, a CMOS sensor, a scintillator, a linear array photodiode, a position sensitive photodiode, and a planar array photodiode.

18. The apparatus of claim 14, wherein the reflecting surface comprises a reflective coating on one side of the flat disc.

19. The apparatus of claim 14, wherein the cylindrical shaft is a linearly displaceable shaft, and the reflecting surface comprises a wedge disposed on one longitudinal surface of the displaceable shaft.

20. The apparatus of claim 19, wherein the wedge translates the vertical motion of the flat disc to horizontal optical beam motion tracked with the optical transducer.

21. The apparatus of claim 14, wherein:
the optical displacement sensor further comprises a second rigid displacement member coupled to the housing, a second light emitter coupled to the housing, and a second optical transducer coupled to the housing, and
wherein the processor is further configured to measure a relative displacement of the second rigid displacement member with respect to the rigid displacement member.

* * * * *

UNITED STATES PATENT AND TRADEMARK OFFICE
CERTIFICATE OF CORRECTION

| | | |
|---|---|---|
| PATENT NO. | : 8,795,205 B2 | Page 1 of 1 |
| APPLICATION NO. | : 13/097908 | |
| DATED | : August 5, 2014 | |
| INVENTOR(S) | : Maity et al. | |

It is certified that error appears in the above-identified patent and that said Letters Patent is hereby corrected as shown below:

In The Specification

In Column 4, Line 32, delete "displacement member 106" and insert -- displacement member 108 --, therefor.

In The Claims

In Column 8, Line 6, in Claim 1, delete "disc, configured" and insert -- disc configured --, therefor.

Signed and Sealed this
Third Day of February, 2015

Michelle K. Lee
*Deputy Director of the United States Patent and Trademark Office*